United States Patent
Steinhuber

(10) Patent No.: US 7,441,897 B2
(45) Date of Patent: Oct. 28, 2008

(54) OPTICAL IMAGING APPARATUS

(76) Inventor: Wolfdietrich Steinhuber, Pertingerweg 10, 6080 Igls (AT)

( * ) Notice: Subject to any disclaimer, the term of this patent is extended or adjusted under 35 U.S.C. 154(b) by 134 days.

(21) Appl. No.: 11/580,803

(22) Filed: Oct. 13, 2006

(65) Prior Publication Data
US 2007/0091267 A1    Apr. 26, 2007

(30) Foreign Application Priority Data
Oct. 14, 2005    (AT)    ............... A 1687/2005

(51) Int. Cl.
*A61B 3/10*    (2006.01)
*A61B 3/12*    (2006.01)
*A61B 3/13*    (2006.01)

(52) U.S. Cl. .............. 351/214; 359/726; 359/223

(58) Field of Classification Search .......... 359/726, 359/732, 223; 351/205–221
See application file for complete search history.

(56) References Cited

U.S. PATENT DOCUMENTS

| | | | |
|---|---|---|---|
| 4,170,398 A | 10/1979 | Koester | |
| 4,991,953 A | 2/1991 | Pflibsen et al. | 351/206 |
| 5,757,463 A | 5/1998 | Kohayakawa | 351/214 |
| 2004/0174498 A1 | 9/2004 | Zorn et al. | |
| 2005/0134797 A1 | 6/2005 | Grove | |

FOREIGN PATENT DOCUMENTS

| | | |
|---|---|---|
| DE | 100 50 358 A1 | 4/2002 |
| WO | 91/08502 | 6/1991 |
| WO | 97/15855 | 5/1997 |

*Primary Examiner*—Darryl J Collins
(74) *Attorney, Agent, or Firm*—Thomas M. Saunders; Seyfarth Shaw LLP

(57) ABSTRACT

An optical imaging apparatus, in particular an ophthalmoscope or microscope or transillumination microscope, comprising a light source arrangement (20) and an illumination beam path (3) which is predetermined at least by an illumination lens arrangement (4), and an observation beam path (11) which is predetermined at least by an observation lens arrangement (12), wherein at least one illumination field aperture (2) is arranged in the illumination beam path (3) and at least one observation field aperture (13) is arranged in the observation beam path (11) and the illumination beam path (3) and the observation beam path (11) are arranged at an angle different from 0° in an illumination image plane (6) in which the illumination field aperture (2) can be imaged by the illumination lens arrangement (4), wherein the illumination lens arrangement (4) and the observation lens arrangement (12) are lens arrangements which are separate from each other, wherein a single light-reflecting mirror body (14) which is oscillatingly reciprocatably pivotable about a pivot axis (15) is arranged in the illumination beam path (3) and in the observation beam path (11).

26 Claims, 6 Drawing Sheets

OPTICAL IMAGING APPARATUS

RELATED APPLICATIONS

Figure 1:
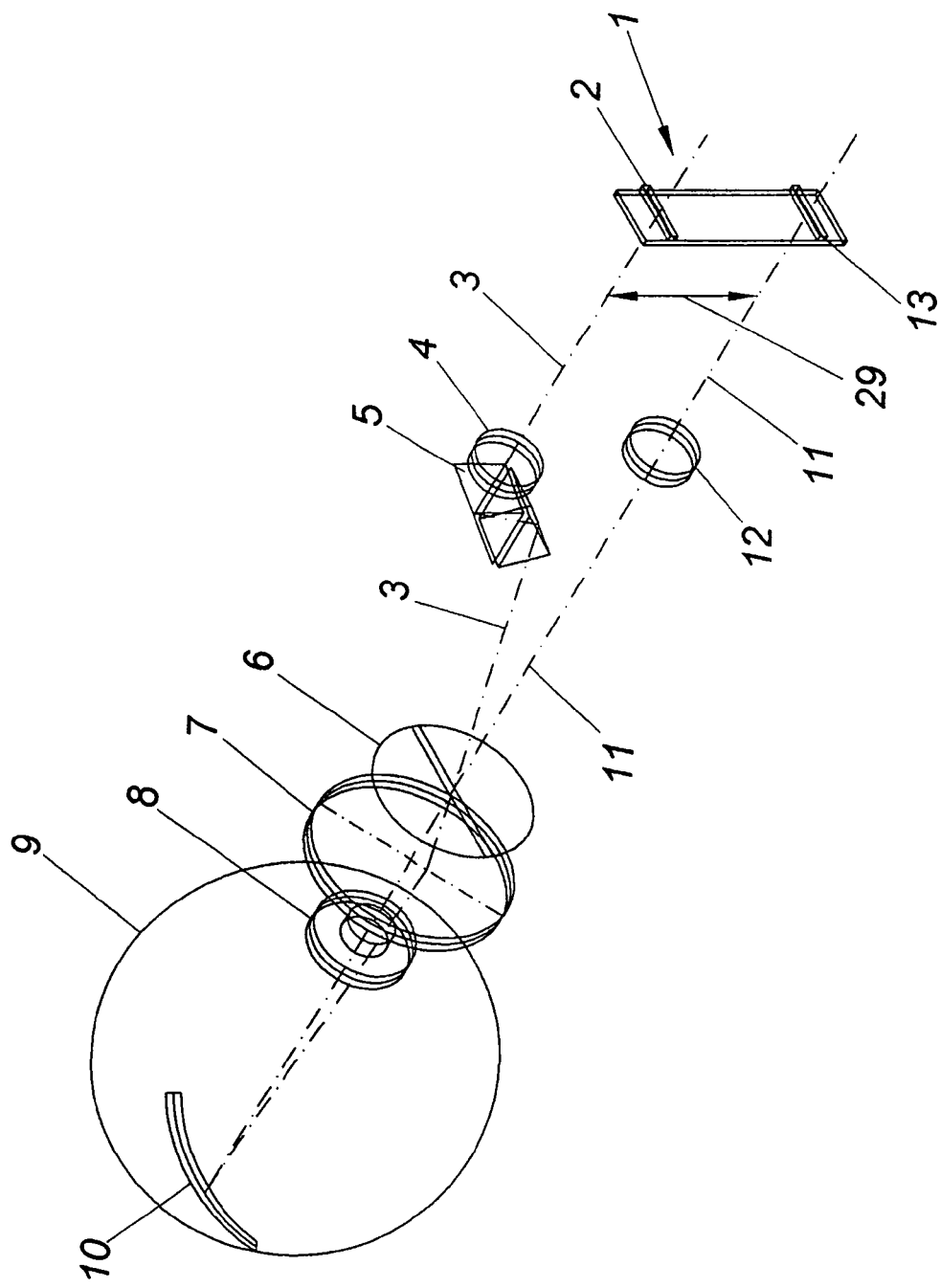

This application is a claims priority from Austrian Application No: A 1687/2005, filed Oct. 14, 2005, entitled OPTICAL IMAGING APPARATUS which is incorporated herein by reference.

The present invention concerns an optical imaging apparatus, in particular an ophthalmoscope or microscope or transillumination microscope, comprising a light source arrangement and an illumination beam path which is predetermined at least by an illumination lens arrangement, and an observation beam path which is predetermined at least by an observation lens arrangement, wherein at least one illumination field aperture is arranged in the illumination beam path and at least one observation field aperture is arranged in the observation beam path and the illumination beam path and the observation beam path are arranged at an angle different from 0° in an illumination image plane in which the illumination field aperture can be imaged by the illumination lens arrangement, wherein the illumination lens arrangement and the observation lens arrangement are lens arrangements which are separate from each other.

Optical apparatuses of the general kind set forth are known in the state of the art for example from WO 97/15855 and DE 10050358. In those specifications in the illustrated embodiments field apertures for delimiting the observation and illumination beam image respectively are arranged both in the observation beam path and also in the illumination beam path. In that case, to achieve optimum imaging, it is necessary for both the opening of the observation field aperture and also that of the illumination field aperture to be arranged with respect to the respective lens arrangement in the image plane of the object to be imaged. Joint oscillation of the two field apertures openings provides that the object to be observed is optically scanned, preferably in strip-wise manner. With a suitably fast movement of the field apertures, that ultimately provides for the human eye an image which is composed of the individual scanned portions or strips. In order to keep the relative spacings between the two field apertures openings constant during the oscillating movement, it is generally conventional for the observation and the illumination field apertures to be constructed in one structural unit.

US 2004/0174498 A1 discloses an ophthalmoscope in which a respective oscillating field aperture is provided in each of the observation beam path and the illumination beam path. The two field apertures are coupled together and arranged in a region in which the illumination beam path and the observation beam path extend substantially parallel to each other. Mutually separate optical systems are also arranged in that region in the illumination and the observation beam paths. So that the observation and the illumination beam paths can intersect in an image plane, that arrangement has a common front lens for the two beam paths.

A disadvantage of the state of the art is that, in the oscillating movement of the field apertures, in particular due to the desired fast movement, inertia forces which cannot be disregarded occur, which in turn cause the entire apparatus to oscillate and vibrate, whereby ultimately the quality of the image produced can suffer as a result.

Therefore the object of the invention is to provide an alternative for the, preferably strip-wise, optical scanning of the object to be imaged, in which the apparatus is less caused to vibrate and oscillate.

In accordance with the invention that is achieved in that a single light-reflecting mirror body which is oscillatingly reciprocatably pivotable about a pivot axis is arranged in the illumination beam path and in the observation beam path.

The mirror body which is reciprocatably pivotable oscillatingly about a pivot axis provides that the object to be imaged or an intermediate image can be scanned thereby. In that situation, upon oscillation of the mirror body, only very slight inertia forces occur so that in operation the apparatus according to the invention is caused to vibrate and oscillate to a lesser degree or in such a way as not to be perceptible. That increases the quality of the images overall, in addition to the inclined illumination in the general fashion set forth, and the use of mutually separate illumination and observation lens arrangements. Synchronisation is automatically achieved by the use of only one mirror body for the illumination and the observation beam paths. Furthermore it is possible to dispense with a movement of the observation and illumination field aperture. They can therefore be of a rigid nature, whereby the oscillations caused by them in the state of the art are avoided.

A particularly advantageous solution provides that the reciprocatably oscillatingly pivotable mirror body is part of a mirror galvanometer and the pivotal drive of the mirror body therefore operates on the basis of the principle of a galvanometer.

Figure 2:
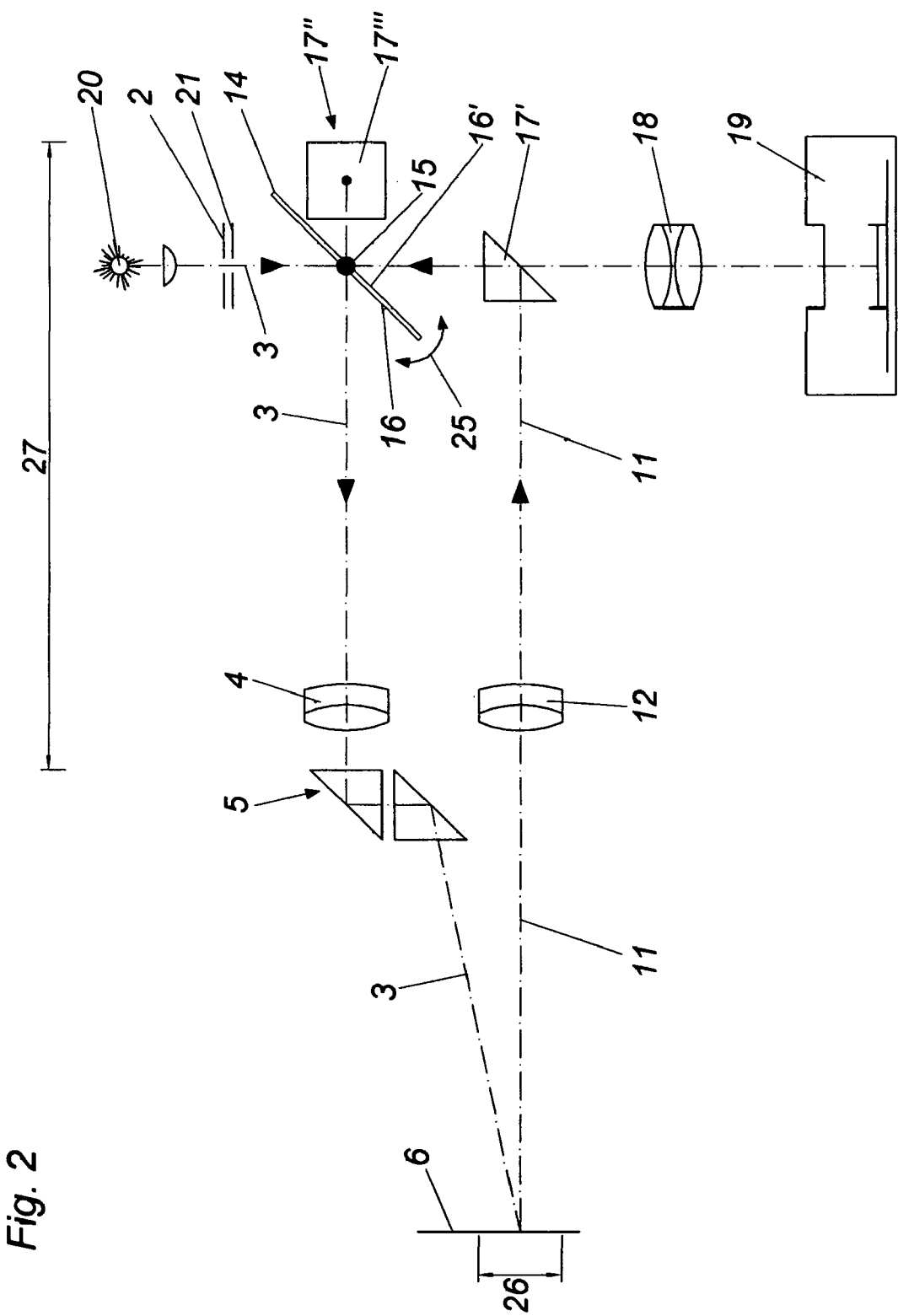
Figure 3:
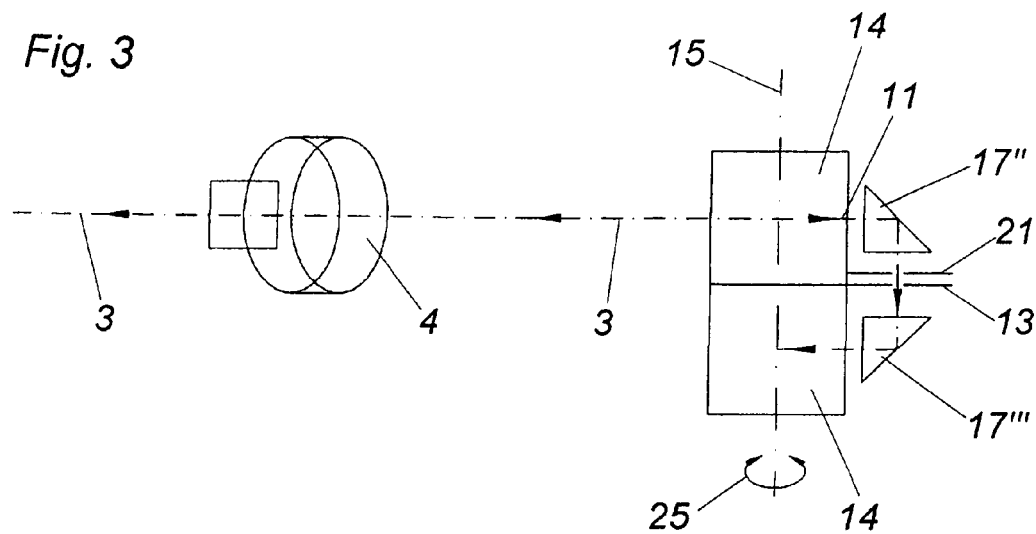
Figure 4:
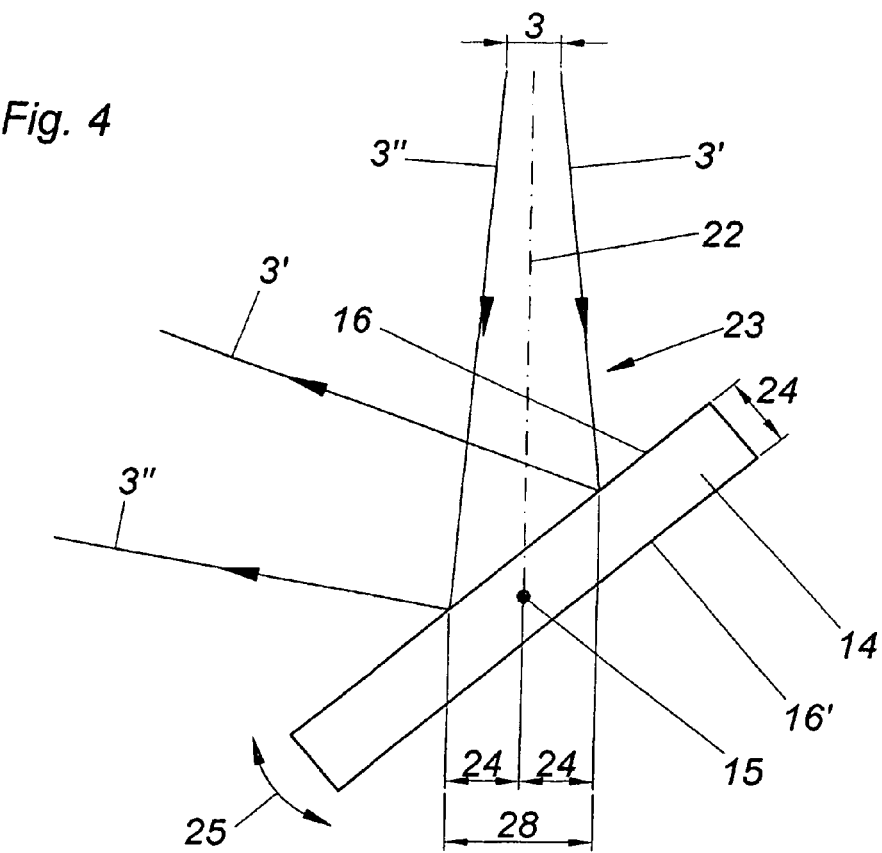
Figure 5:
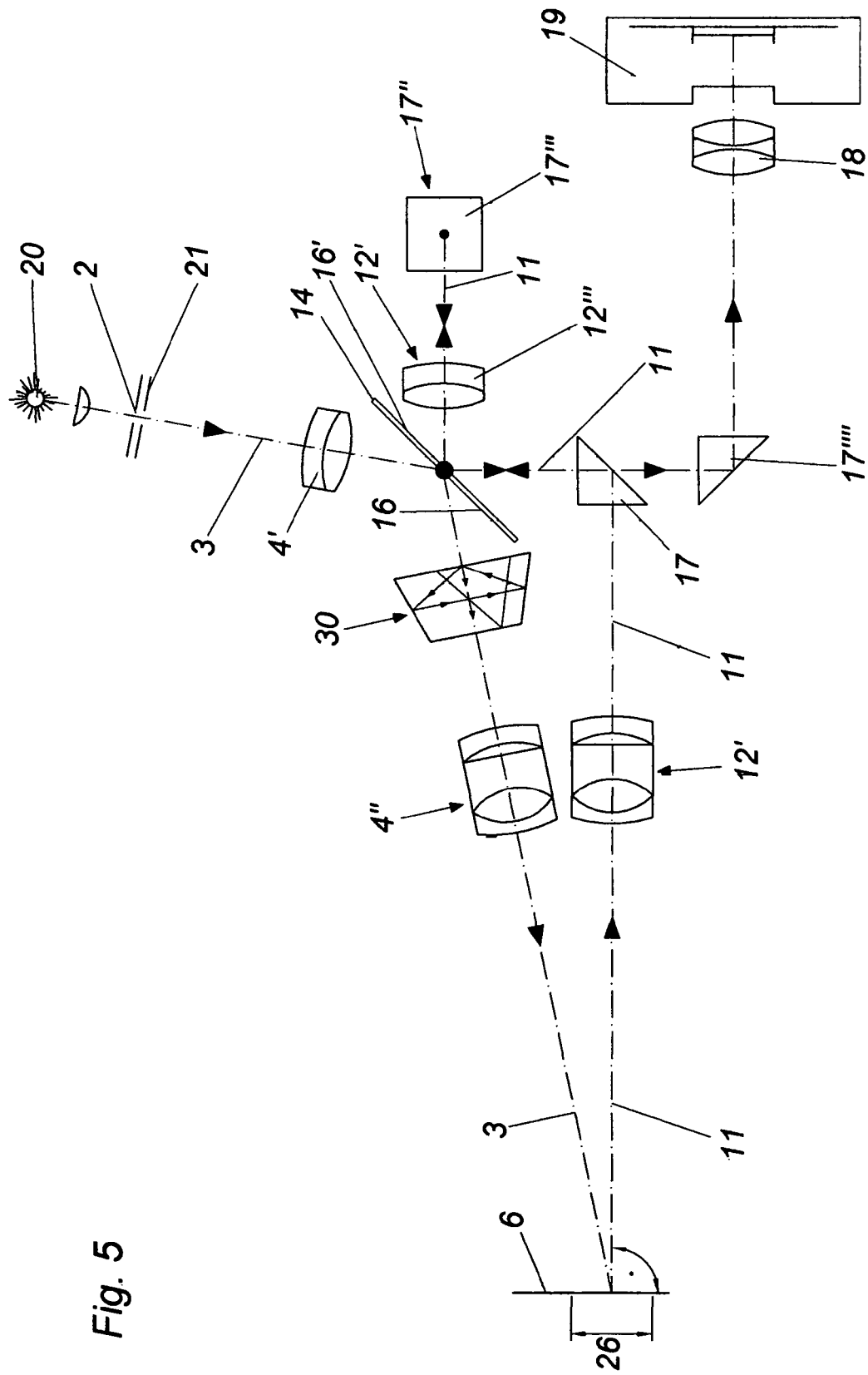
Figure 6:
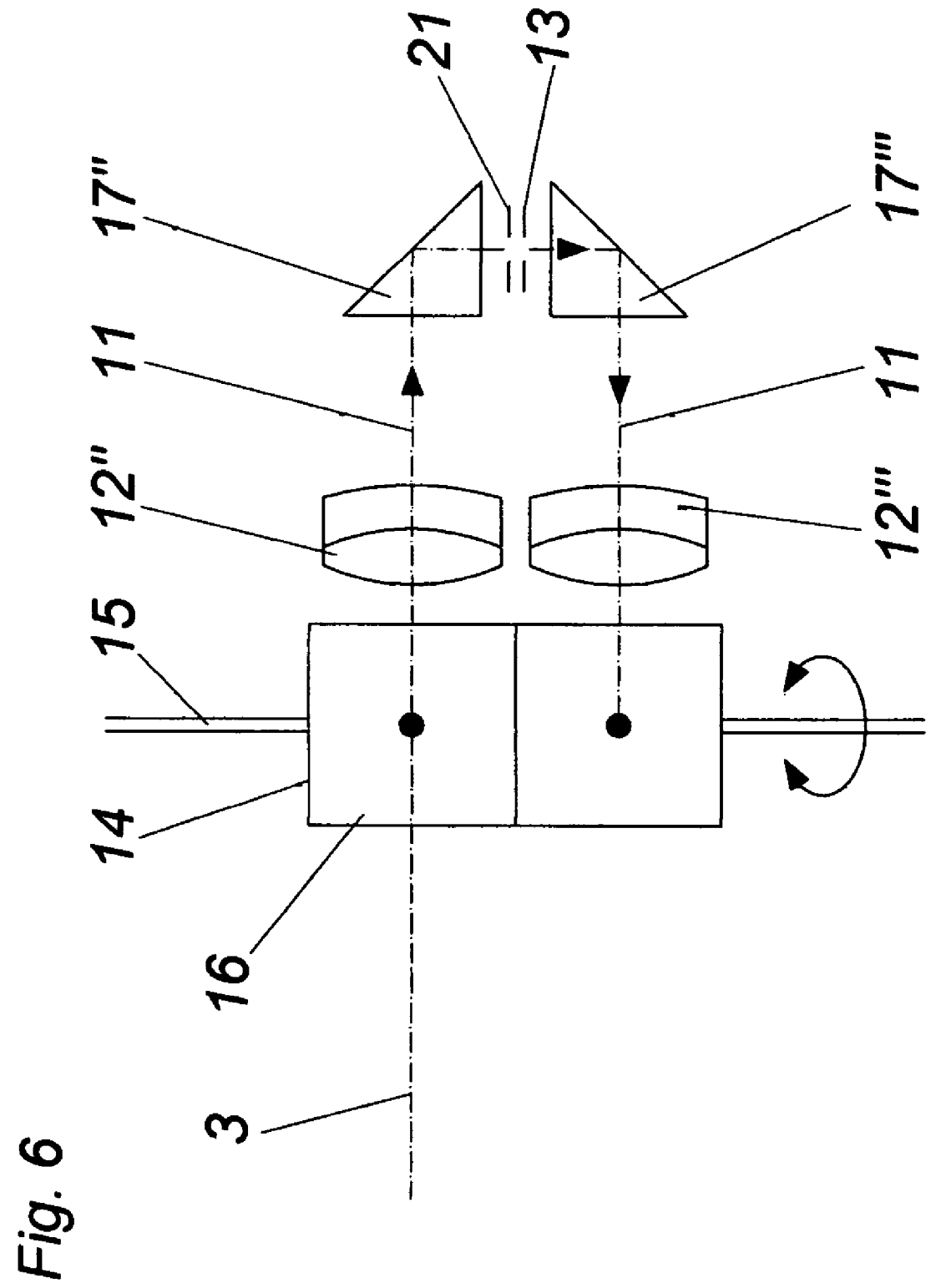
Figure 7:
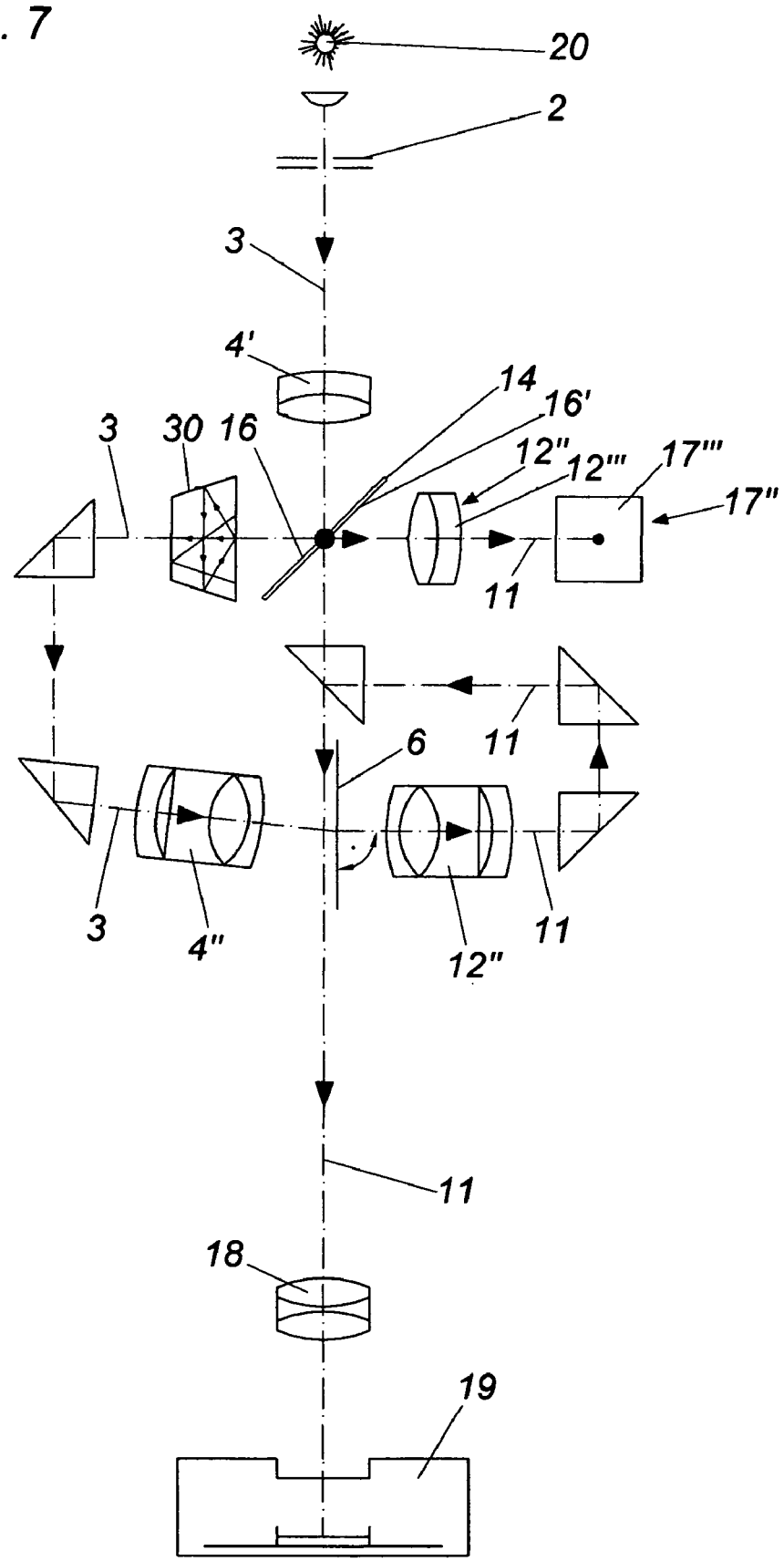

Further details and features of the present invention will be apparent from the specific description. In the drawing:

FIG. 1 is a diagrammatic representation of an ophthalmoscope in accordance with the state of the art, FIG. 2 is a side view showing a diagrammatic representation of a first embodiment according to the invention, FIG. 3 is a detail representation from FIG. 2 as a plan view on to the mirror body, FIG. 4 is a side view showing a detail representation relating to the mirror body of FIG. 2, FIG. 5 is a side view showing a diagrammatic representation of a second embodiment according to the invention, FIG. 6 is a detail representation from FIG. 5 as a plan view on to the mirror body, and FIG. 7 is a diagrammatic representation of a third embodiment according to the invention.

In the state of the art shown in FIG. 1 the retina 10 of the eye, as the object to be imaged, is scanned or illuminated line-wise by means of an ophthalmoscope. Light of a light source (not shown) passes along the illumination beam path 3 through the opening of the illumination field aperture 2 in the illumination beam path 3 into the illumination objective (illumination lens arrangement) 4 and is deflected in a controlled and preferably adjustable prism system 5 in such a way that the illumination beam path 3 coincides in the intermediate image plane 6 with the observation beam path 11 at an angle different from 0°. In that respect reference is made to inclined illumination. In that case the intermediate image plane 6 is the illumination image plane in which the illumination field aperture 2 is imaged by the illumination lens arrangement 4. Subsequently to approximately parallel positioning of the incoming light beam in the ophthalmoscopy magnifying lens 7 the light beam passes through the pupil 8 into the eye 9 and illuminates the illustrated light strips on the retina 10. The light which is diffracted there is reflected back along the observation beam path 11 and, after passing through the observation objective (observation lens arrangement) 12 and the observation field aperture 13 can be detected with an optical sensor (for example the eye of a physician). The light strip 10 is displaced on the retina by virtue of the oscillating movement of the double aperture 1. In that case, the illumination field aperture 2 and the observation field aperture 13 are combined to afford a structural unit in the double aperture 1. If now the double aperture 1 oscillates in the direction of movement 29 at a suitably high frequency (for example 50 Hertz), that provides a cohesive image of the retina 10 of the eye 9 being observed, for a human eye (or a corresponding sensor) which receives the light from the observation beam path 11 in the opening of the observation field aperture 13.

The object to be imaged as well as the illumination lens arrangement 4 and the illumination field aperture 2 are arranged in that case in such a way that the illumination field aperture 2 is imaged by way of the lens arrangement 4 into the illumination image plane 6 and thus on to the object of which the image is to be formed. That affords specifically targeted illumination of the object to be imaged, such illumination corresponding region-wise to the shape of the opening of the illumination field aperture 2. In that respect it is immaterial whether the object to be imaged is disposed directly in the illumination image plane 6 or whether the object to be imaged is present in the form of a real intermediate image in the illumination image plane 6 as in FIG. 1. Imaging of the object in the illumination image plane 6 can be effected for example as shown in FIG. 1 by means of an ophthalmoscopy magnifying lens 7.

The object to be imaged which is illuminated as set forth hereinbefore is imaged on the observation image plane by way of the observation beam path 11 and the observation lens arrangement 12 (here once again in the form of a simple converging lens). In that respect it is known in the state of the art for an observation field aperture 13 to be arranged in the observation image plane. That is preferably also to be implemented in apparatuses in accordance with the invention.

FIG. 2 now shows an embodiment according to the invention of an ophthalmoscope. As also in the state of the art, mutually separate lens arrangements 4 and 12 in the illumination beam path 3 and the observation beam path 11, together with the prism system 5, provide that the illumination beam path 3 and the observation beam path 11 meet at an angle different from 0°, in the illumination image plane 6. The object to be imaged can be arranged directly in the illumination image plane 6, whereby the illumination image plane 6 is then substantially in the plane of the object. That kind of arrangement is advantageous in particular in microscopes according to the invention (reflected light microscope or transillumination microscope). Alternatively—more particularly in the case of ophthalmoscopes—however a real intermediate image of the object to be observed, for example the retina 10, can also be produced in the illumination image plane 6, as shown in FIG. 1. The illumination field aperture 2 and the observation field aperture 13 which is to be seen in the plan view in FIG. 3 are preferably of a rigid nature, that is to say not movable—in the sense of stationary—, whereby the undesired vibrations and oscillations in the ophthalmoscope as occur in the state of the art by virtue of the movement of the field apertures 2 and 13 are prevented. The light source arrangement 20 is provided for illumination purposes. That desirably comprises a flash light. The mirror body 14 which is now provided in accordance with the invention and which is reciprocatably oscillatingly pivotable about the pivot axis 15 in the direction of the arrows 25, by virtue of its oscillating movement, provides for scanning of the object to be observed or the illumination image plane 6.

Both the illumination field aperture 2 and also the observation field aperture 13 are preferably of a slit-shaped nature, with the result that the illumination image plane 6 is scanned in strip form. In order to compensate for unequal distribution of the light intensity along the illuminated strip, which may possibly occur due to the inclined illumination, it can be provided that the slits in the field apertures 2 and 13 are of a V-shaped configuration. In this embodiment and in the embodiments set forth hereinafter in accordance with the invention the illumination field aperture 2 and/or the observation field aperture 13, like also spatial filter apertures 21 which can possibly be provided, can be adapted to be adjustable in respect of their opening width. It is appropriate in that respect if the above-mentioned field apertures 2 and/or 13 and/or 21 are adjustable in mutually coupled relationship, whereby adjustment of the individual field apertures is automatically matched to each other.

In the illustrated embodiment the light on the way from the light source arrangement 20 to the surface scanner 19 passes on to the mirror body 14 a total of three times. In that respect the first reflection occurs in the illumination beam path 3 at the upper reflecting surface 16 of the mirror body 14 on the way from the illumination field aperture 2 to the illumination lens arrangement 4. In the observation beam path 11, the light is then firstly deflected with a deflection prism 17' on to the lower reflecting surface 16' of the mirror body 14 in order from there to impinge on the deflection prism 17" (see FIG. 3). There the light is again reflected in order then to pass through the observation field aperture 13 to a third deflection prism 17'''. Therein the light is again deflected on to the lower reflecting surface 16' of the mirror body 14. There, reflection takes place in the direction of the lens arrangement 18 connected upstream of the surface scanner 19. In that case the lens arrangement 18 is so designed that the real intermediate image which is produced in the plane of the observation field aperture 13 is imaged in the form of a real image into the receiving plane of the surface scanner 19. All optical components except for the mirror body 14 can be of a rigid nature in that case. Scanning of the illumination image plane is effected exclusively by way of the oscillating pivotal movement of the mirror body 14.

The use of a single mirror body for the illumination beam path 3 and the observation beam path 11 provides that the required synchronisation for correct imaging of the surface 26 to be imaged (in the illumination image plane 6) on the surface scanner 19 is automatically afforded.

The length of the optical beam distance between the illumination field aperture 2 and the surface 16 of the mirror body 14, which reflects the light of the illumination beam path 3, desirably corresponds to the length of the optical beam distance between the surface 16' of the mirror body 14, which reflects the light of the observation beam path 11, and the observation field aperture 13. The optical beam distance between the observation field aperture 13 and the reflecting surface 16' through the deflection prism 17''' should also be of the same length. It will also be appreciated that the deflection prisms 17', 17" and 17''' can also be replaced by corresponding mirrors.

In the case of optical imaging apparatuses, distortions of the definitive image sometimes occur due to defective imagings of higher diffraction orders. In order to avoid this, it is possible to provide spatial filters which are arranged outside the image planes—for example in the form of further apertures 21 with slit-shaped passage apertures—, as is known per se in the state of the art. Arranging the apertures 21 outside the image planes provides that higher diffraction orders are masked out so that no aberration phenomena can occur as a result thereof. The spatial filter or filters is or are arranged preferably stationarily in the optical imaging apparatus.

In order to illuminate the surface 26 which is to be imaged as uniformly as possible and to image it in a correspondingly uniformly illuminated fashion, it is desirably to be provided that the pivotal drive (which is not explicitly shown here) for the mirror body 14 makes it possible for the mirror body 14 to be reciprocatably oscillatingly pivoted in such a way that the light of the illumination beam path 13 passes over a surface to be imaged, in the illumination image plane 6, at a substantially constant speed. The pivotal drive can engage the pivot spindle 15 directly or by way of a transmission. A desirable variant provides that a galvanometer is used as the pivotal drive.

If in accordance with a preferred embodiment the light source arrangement has a flash light source, suitable synchronisation between the light source 20, the pivotal movement of the mirror body 14 and recording by the surface scanner 19 is to be provided. That can be achieved by the flash light source and the pivotal drive of the mirror body 14 and the surface scanner 19 being matched to each other in such a way that, during the duration of a flash of the flash light source, the mirror body 14 is pivotable at least once to such an extent that the surface 26 to be imaged in the illumination image plane 6 can be completely traversed once and that the surface scanner 19 completely receives the image impinging thereon.

In relation to FIG. 3 it should also be noted that this is a plan view on to the portion 26 shown in FIG. 2. In this case the light source arrangement 20, the illumination field aperture 2 and the spatial filter 21 arranged therebeneath are not shown in order to permit a direct view on to the mirror body 14, the deflection prisms 17" and 17''' and the observation field aperture 13 and the spatial filter aperture 21. If FIG. 3 is considered, the light coming from the light source arrangement 20 or illumination field aperture 2 impinges perpendicularly from above on to the upper reflecting surface 16 of the mirror body 14 and is then reflected in the direction of the illumination beam path 3. On the way back along the observation beam path 11 the light impinges from below on to the reflecting surface 16' of the mirror body 14 and is reflected in the direction of the deflection prism 17" in order then to cover the distance, which has already been described, through the observation field aperture 13 back to the lower surface 16' of the mirror body 14. There reflection occurs in the direction of the lens arrangement 18. The beam configuration which extends beneath the mirror body 14 and which is actually not visible in the plan view is shown in broken line.

It is also possible to see from FIG. 3 that the beam configuration in the observation beam path 11 from the first deflection prism 17' to the mirror body 14 is displaced laterally with respect to the beam configuration from the mirror body 14 to the lens arrangement 18.

FIG. 4 once again shows on an enlarged scale a light beam 23 coming from the illumination field aperture 2. Besides the center 22 shown in broken line of the light beam 23, it is also possible to see the edge beams 3' and 3". In that case the light beam desirably impinges on the mirror body 14 in such a way that the center 22 meets the mirror body 14 substantially in the region of the pivot axis 15. That is generally to be assumed if the center 22 of the light beam 23 produced impinges on the mirror body 14 no further away from the pivot axis 15 than the smallest spacing 24 between the light-reflecting surfaces 16 and 16' of the mirror body 14. That region 28 is explicitly shown in FIG. 4. Furthermore FIG. 4 also shows that, in a preferred embodiment of the mirror body 14, it is provided that it has precisely two flat light-reflecting surfaces 16 and 16' on two oppositely disposed outside faces. The light-reflecting surfaces 16 and 16' are preferably arranged in mutually parallel relationship.

FIG. 5 shows a second embodiment according to the invention in the form of an ophthalmoscope which in its basic structure is similar to that shown in FIG. 2. In this case also the illumination beam path 3 meets the surface 26 to be imaged or the illumination image plane 6 at an angle different from 90° while the observation beam path 11 extends substantially perpendicularly, that is to say in the form of a normal, on to the surface 26 to be imaged. That arrangement of the observation beam path 11 guarantees optimum depth of focus in imaging of the surface 26 to be imaged. That depth of focus would not be afforded over the entire surface 26 to be imaged in the case of an arrangement differing from 90°, as between the surface 26 or the object plane and the observation beam path 11.

In contrast to FIG. 2, the embodiment shown in FIG. 5 provides that a reversal prism 30 is arranged in the illumination beam path 3 instead of the prisms 5. Reversal systems are known per se in the state of the art and serve for image reversal through 180°. The reversal system 30 used can be for example Pechan prisms which are known in the state of the art, with a roof edge configuration, or so-called Porro systems. The reversal system 30, instead of it being arranged in the illumination beam path 3, can also be disposed in the observation beam path 11.

A further difference in relation to FIG. 2 is that both the illumination lens arrangement 4 and also the observation lens arrangement 12 each have at least two spatially mutually separate lens 4' and 4" and 12' and 12". The lenses 4' and 12' respectively produce parallel beams in the illumination beam path 3 and in the observation beam path 11 respectively while the lenses 4" and 12" in turn convert those parallel beams into convergent light beams. In the side view adopted in FIG. 5 the lens 12" is concealed by the lens 12''' and cannot therefore be seen directly. In that respect attention is directed to FIG. 6 which is briefly described once again hereinafter. The lens 12''' in turn produces parallel beams which are again converted by the lens arrangement 18 to a convergent beam with a focal point on the surface scanner 9. That arrangement of the lenses in the illumination beam path 3 and the observation beam path 11 ensures that there are always parallel beams in the region of the mirror body 14, which overall enhances the imaging quality. It is therefore desirable if the mirror body 14 is arranged in the region of the parallel beams between the separate lenses 4', 4", 12', 12", 12''' and 18.

FIG. 6 is a plan view showing the arrangement of the observation field aperture 13 between the two deflection prisms 17" and 17'''. The illumination beam path 3 is reflected at the top side 16 of the mirror body 14. The light of the observation beam path 11 impinges from below on the oppositely disposed reflecting surface 16' of the mirror body 14 and is converted by the lens 12" into a convergent beam which is deflected by means of the deflection prism 17" through the spatial filter aperture 21 into the observation image plane arranged in the region of the observation field aperture 13. From there the observation beam path 11 again extends in the direction of the lower reflecting surface 16" of the mirror body 14 and is deflected in the direction of the deflection prism 17''''. The further beam configuration in the direction of the surface scanner 19 is again to be seen in FIG. 5. The selected arrangement, as also in the case of the embodiment of FIG. 2, ensures that the illumination beam path 3, in particular between the light source arrangement 20 or the illumination field aperture 2 and the illumination image plane 6, extends completely separately from the observation beam path 11, preferably between the illumination image plane 6 and the observation field plane 13 or an optical sensor or surface scanner 19. The same applies for the first subsection of the observation beam path 11 between the illumination image plane 6 and the observation field aperture 13 and the second subsection of the observation beam path 11 between the observation field aperture 13 and an optical sensor or surface scanner 19. There are therefore three completely mutually separate beam paths, thereby providing a particularly sharp-contrast image of the object to be investigated. In that respect the expression completely separate beam paths is used in particular to denote that the said beam paths neither intersect nor overlap nor have any common subsection. That ensures the high levels of contrast which are required for example for eye examination.

FIG. 7 shows a third embodiment in accordance with the invention in the form of a diagrammatically illustrated transillumination microscope. The observation beam path 3 impinges at an angle differing from the normal or perpendicular, on to the object which is to be observed or transilluminated and which is arranged in the illumination field plane or object plane 16. The observation beam path 11 in contrast is again arranged in a normal, that is to say perpendicularly on to the illumination image plane or object plane 6. In this embodiment also there is therefore once again an angle differing from 0° between the illumination beam path 3 and the observation beam path 11. As in the embodiment of FIG. 5, this embodiment also has separate lenses 4' and 4" for the illumination beam path and 12', 12", 12''' and 18 for the observation beam path 11. As shown in FIG. 6 the lens 12" is concealed behind the lens 12''' in the side view adopted in FIG. 7. In this case also once again there are three spatially completely mutually separate beam paths. The first is again the illumination beam path 3 between the light source arrangement 20 and the illumination image plane 6. The second beam path is the first subsection of the observation beam path 11 between the illumination image plane 6 and the observation field aperture 13. The third beam path is the second subsection of the observation beam path 11 between the observation field aperture 13 and the surface scanner 19. If necessary, in the case of the transillumination microscope shown in FIG. 7 also a reversal system 30 shown here in the illumination beam path 3 can be arranged both in the illumination beam path 3 and also in the observation beam path 11.

In all three embodiments according to the invention as shown in FIGS. 2 through 7 the illumination beam path 3 impinges from above on to the reflecting surface 16 of the oscillating mirror body 14 while the observation beam path 11 impinges twice in the form of two spatially separate reflection regions from below on to the lower reflecting surface 16' of the mirror body 14.

Alternatively however it would also be possible for embodiments to be designed in such a way that all three mirror reflections take place only at the upper reflection surface 16 or only at the lower reflection surface 16' of the mirror body 14. Furthermore it is also possible to envisage embodiments in which there is provided for each mirror reflection its own reflection surface, that is to say for example a mirror body 14 with three reflection surfaces. Other hybrid forms are also possible as long as a single pivotable mirror body 14 is arranged in the illumination beam path 3 and in the observation beam path 11, which ensures the above-mentioned synchronisation effect.

The apparatuses according to the invention, when suitably designed, can be operated with light from the entire light wavelength range. Preferably visible light is involved. However other wavelength ranges are also possible. In order to ensure reconstruction of the individual scanned portions or strips to provide a total image, it is desirable to select an oscillation frequency for the mirror body 14 of at least 50 Hz. Higher frequencies lead to a further improvement in the resulting imaging. Instead of the preferably digital surface scanner 19 it will be appreciated that it is also possible to use other cameras and the like. It will be appreciated that it is further possible directly to view images occurring subsequently to the lens arrangement 18. The (reflected light) microscopes which are not shown here in the form of an embodiment specific thereto can be implemented in the points which are essential to the invention like ophthalmoscopes.

The invention claimed is:

1. An optical imaging apparatus comprising a light source arrangement and an illumination beam path which is predetermined at least by an illumination lens arrangement, and an observation beam path which is predetermined at least by an observation lens arrangement, wherein at least one illumination field aperture is arranged in the illumination beam path and at least one observation field aperture is arranged in the observation beam path and the illumination beam path and the observation beam path are arranged at an angle different from 0° in an illumination image plane in which the illumination field aperture can be imaged by the illumination lens arrangement, wherein the illumination lens arrangement and the observation lens arrangement are lens arrangements which are separate from each other, characterised in that a single light-reflecting mirror body which is oscillatingly reciprocatably pivotable about a pivot axis is arranged in the illumination beam path and in the observation beam path.

2. An optical imaging apparatus as set forth in claim 1 characterised in that the mirror body has at least two or precisely two flat light-reflecting surfaces on possibly two mutually oppositely disposed outside faces.

3. An optical imaging apparatus as set forth in claim 2 characterised in that the light-reflecting surfaces are arranged in mutually parallel relationship.

4. An optical imaging apparatus as set forth in claim 1 characterised in that the mirror body is part of a mirror galvanometer.

5. An optical imaging apparatus as set forth in claim 1 characterised in that the mirror body or its pivot axis are arranged in such a way that in the illumination beam path the center of a light beam produced by means of the light source arrangement and the illumination field aperture impinges on the mirror body substantially in the region of the pivot axis.

6. An optical imaging apparatus as set forth in claim 5 characterised in that the center of the light beam produced impinges on the mirror body no further away from the pivot axis than the smallest spacing between the light-reflecting surfaces of the mirror body.

7. An optical imaging apparatus as set forth in claim 1 characterised in that the illumination field aperture or the observation field aperture have substantially slit-shaped passage openings for light.

8. An optical imaging apparatus as set forth in claim 7 characterised in that the slit-shaped passage openings are of a V-shaped configuration.

9. An optical imaging apparatus as set forth in claim 1 characterised in that the optical imaging apparatus is so designed that the light of the light source arrangement on the illumination beam path is reflected once at the mirror body and on the observation beam path is reflected twice at the mirror body.

10. An optical imaging apparatus as set forth in claim 1 characterised in that the length of the optical beam distance between the illumination field aperture and the surface of the mirror body which reflects the light of the illumination beam path corresponds to the length of the optical beam distance between the surface of the mirror body which reflects the light of the observation beam path and the observation field aperture and the length of the optical beam distance between the observation field aperture and the surface of the mirror body which reflects the light of the illumination beam path.

11. An optical imaging apparatus as set forth in claim 1 characterised in that at least one spatial filter is arranged outside the image planes of the optical imaging apparatus.

12. An optical imaging apparatus as set forth in claim 11 characterised in that the spatial filter is in the form of an aperture with a substantially slit-shaped passage opening.

13. An optical imaging apparatus as set forth in claim 1 characterised in that there is provided a lens arrangement for imaging an image produced in the observation field aperture on a surface scanner.

14. An optical imaging apparatus as set forth in claim 1 characterised in that there is provided a pivotal drive for the mirror body, which makes it possible for the mirror body to be oscillatingly reciprocatably pivoted in such a way that the light of the illumination beam path passes over a surface to be imaged in the illumination image plane at a substantially constant speed.

15. An optical imaging apparatus as set forth in claim 1 characterised in that the light source arrangement has a flash light source.

16. An optical imaging apparatus as set forth in any of claims 12, 13 or 14 characterised in that the flash light source and the pivotal drive of the mirror body and the surface scanner are synchronised in such a way that during the duration of a flash of the flash light source the mirror body can be pivoted at least once to such an extent that the surface to be imaged can be completely passed over once in the illumination image plane and that the surface scanner completely receives the image impinging thereon.

17. An optical imaging apparatus as set forth in claim 1 characterised in that a first deflection prism or a first mirror and a second deflection prism or a second mirror are so arranged that the light on the observation beam path coming from the mirror body can be reflected by the first deflection prism or the first mirror to the observation field aperture and further by the second deflection prism or the second mirror towards the mirror body.

18. An optical imaging apparatus as set forth in claim 1 characterised in that the observation beam path extends substantially perpendicularly to the surface to be imaged or the object plane or as a normal to the surface to be imaged or the object plane.

19. An optical imaging apparatus as set forth in claim 1 characterised in that the illumination beam path between the light source arrangement or the illumination field aperture and the illumination image plane extends completely separately from the observation beam path between the illumination image plane and the observation field aperture or an optical sensor or surface scanner.

20. An optical imaging apparatus as set forth in claim 1 characterised in that a first subsection of the observation beam path between the illumination image plane and the observation field aperture extends completely separately from a second subsection of the observation beam path between the observation field aperture and an optical sensor or surface scanner.

21. An optical imaging apparatus as set forth in claim 1 characterised in that at least one lens arrangement, selected from a group consisting of the illumination lens arrangement and the observation lens arrangement, respectively have at least two spatially mutually separate lenses, wherein respective parallel beams extend between the separate lenses.

22. An optical imaging apparatus as set forth in claim 20 characterised in that the mirror body is arranged in the region of parallel beams between the separate lenses of the illumination lens arrangement or between the separate lenses of the observation lens arrangement.

23. An optical imaging apparatus as set forth in claim 1 characterised in that a reversal system is arranged in the illumination beam path or in the observation beam path.

24. An optical imaging apparatus as set forth in claim 1 characterised in that at least one aperture selected from a group consisting of the illumination field aperture and the observation field aperture and the spatial filter aperture is adjustable in respect of its aperture opening width.

25. An optical imaging apparatus as set forth in claim 1 characterised in that at least two apertures selected from a group consisting of the illumination field aperture and the observation field aperture and the spatial filter aperture are adjustable in mutually coupled relationship in respect of their aperture opening width.

26. An optical imaging apparatus as set forth in claim 1 characterised in that it is an ophthalmoscope or a reflected light microscope or a transillumination microscope.

* * * * *